Figure 1:
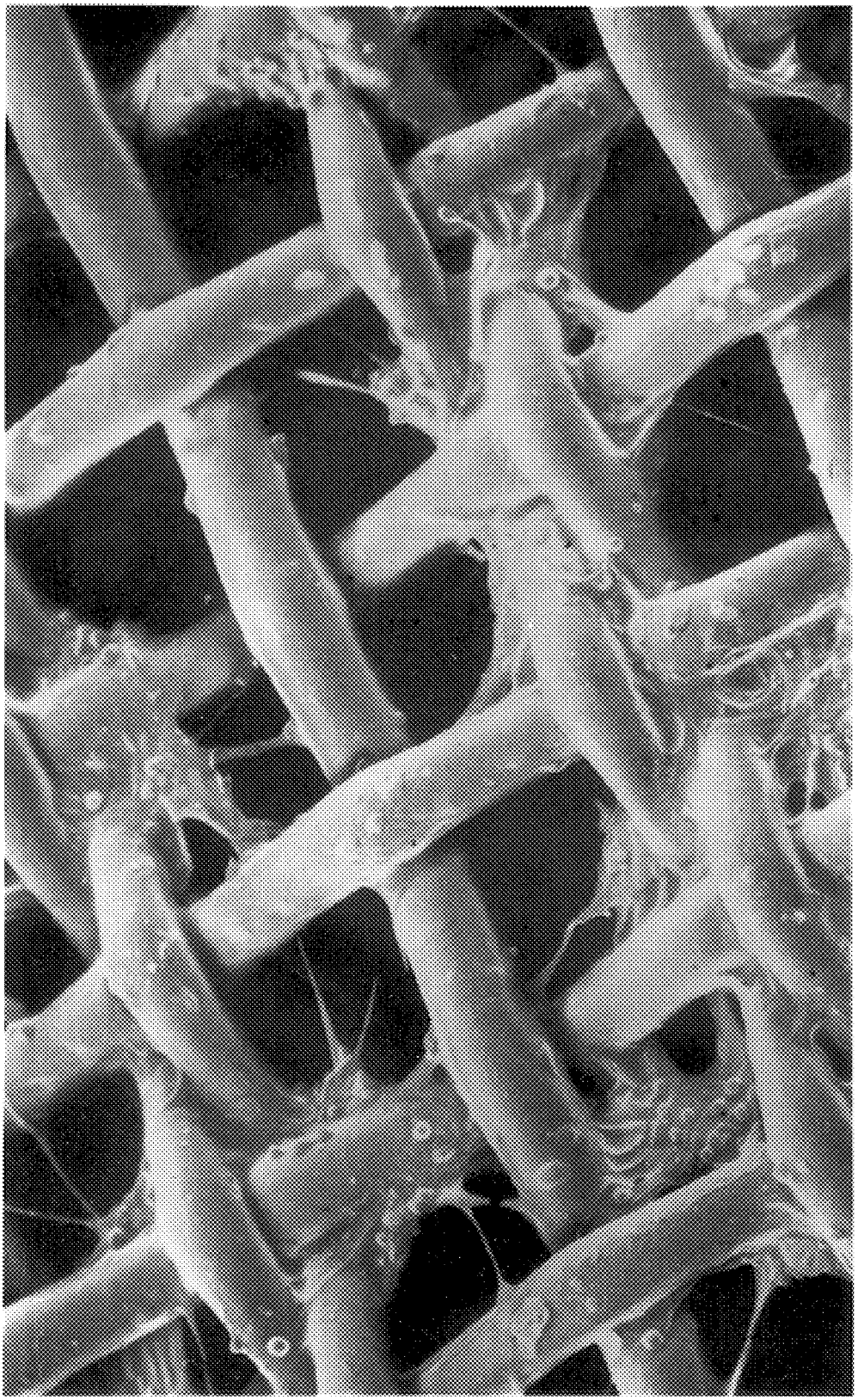

United States Patent [19]
Naughton et al.

[11] Patent Number: 6,022,743
[45] Date of Patent: *Feb. 8, 2000

[54] THREE-DIMENSIONAL CULTURE OF PANCREATIC PARENCHYMAL CELLS CULTURED LIVING STROMAL TISSUE PREPARED IN VITRO

[75] Inventors: Gail K. Naughton, Del Mar; Brian A. Naughton, El Cajon, both of Calif.

[73] Assignee: Advanced Tissue Sciences, Inc., La Jolla, Calif.

[*] Notice: This patent is subject to a terminal disclaimer.

[21] Appl. No.: 09/264,513

[22] Filed: Mar. 8, 1999

Related U.S. Application Data

[63] Continuation of application No. 09/237,980, Jan. 25, 1999, which is a continuation of application No. 08/487,749, Jun. 7, 1995, Pat. No. 5,863,531, which is a continuation-in-part of application No. 08/254,096, Jun. 6, 1994, abandoned, which is a continuation-in-part of application No. 08/131,361, Oct. 4, 1993, Pat. No. 5,443,950, which is a division of application No. 07/575,518, Aug. 30, 1990, Pat. No. 5,266,480, which is a division of application No. 07/402,104, Sep. 1, 1989, Pat. No. 5,032,508, which is a continuation-in-part of application No. 07/242,096, Sep. 8, 1988, Pat. No. 4,963,489, application No. 07/038,110, Apr. 14, 1987, abandoned, and application No. 07/036,154, Apr. 3, 1987, Pat. No. 4,721,096, which is a continuation of application No. 06/853,569, Apr. 18, 1986, abandoned.

[51] Int. Cl.[7] ............... C12N 5/00; C12N 5/08; C12N 11/08; A61F 2/00
[52] U.S. Cl. .......... 435/395; 424/93.7; 424/423; 435/1.1; 435/178; 435/180; 435/398; 435/399; 435/402
[58] Field of Search .................. 424/93.7, 423; 435/1.1, 174, 178, 180, 182, 395, 398, 399, 402

[56] References Cited

U.S. PATENT DOCUMENTS

| | | | |
|---|---|---|---|
| 4,458,678 | 7/1984 | Yannas et al. | 602/48 |
| 4,963,489 | 10/1990 | Naughton et al. | 435/1.1 |
| 5,032,508 | 7/1991 | Naughton et al. | 435/32 |
| 5,041,138 | 8/1991 | Vacenti et al. | 623/16 |
| 5,160,490 | 11/1992 | Naughton et al. | 435/287.1 |
| 5,266,480 | 11/1993 | Naughton et al. | 435/371 |
| 5,399,665 | 3/1995 | Barrera et al. | 528/354 |
| 5,443,950 | 8/1995 | Naughton et al. | 435/1.1 |
| 5,863,531 | 1/1999 | Naughton et al. | 424/93.7 |

Primary Examiner—David M. Naff
Attorney, Agent, or Firm—Pennie & Edmonds LLP

[57] ABSTRACT

A stromal cell-based three-dimensional cell culture system is prepared which can be used to culture a variety of different cells and tissues in vitro for prolonged periods of time. The stromal cells and connective tissue proteins naturally secreted by the stromal cells attach to and substantially envelope a framework composed of a biocompatible non-living material formed into a three-dimensional structure having interstitial spaces bridged by the stromal cells. The living stromal tissue so formed provides the support, growth factors, and regulatory factors necessary to sustain long-term active proliferation of cells in culture and/or cultures implanted in vivo. When grown in this three-dimensional system, the proliferating cells mature and segregate properly to form components of adult tissues analogous to counterparts in vivo, which can be utilized in the body as a corrective tissue. For example, and not by way of limitation, the three-dimensional cultures can be used to form tubular tissue structures, like those of the gastrointestinal and genitourinary tracts, as well as blood vessels; tissues for hernia repair and/or tendons and ligaments; etc.

38 Claims, 1 Drawing Sheet

THREE-DIMENSIONAL CULTURE OF PANCREATIC PARENCHYMAL CELLS CULTURED LIVING STROMAL TISSUE PREPARED IN VITRO

This is a Continuation of U.S. patent application Ser. No. 09/237,980, filed Jan. 25, 1999; which is a continuation of Ser. No. 08/487,749, filed Jun. 7, 1995 (U.S. Pat. No. 5,863,531); which is a Continuation-In-Part of Ser. No. 08/254,096, filed Jun. 6, 1994 (abandoned); which is a Continuation-In-Part of Ser. No. 08/131,361, filed Oct. 4, 1993, U.S. Pat. No. 5,443,950; which is a divisional of Ser. No. 07/575,518, filed Aug. 30, 1990, U.S. Pat. No. 5,266,480; which is a division of Ser. No. 07/402,104, filed Sep. 1, 1989, U.S. Pat. No. 5,032,508; which is a continuation-in-part of Ser. No. 07/242,096, filed Sep. 8, 1988, U.S. Pat. No. 4,963,489; which is a continuation-in-part of Ser. No. 07/038,110, filed Apr. 14, 1987, (abandoned); which is a continuation-in-part of Ser. No. 07/036,154, filed Apr. 3, 1987, U.S. Pat. No. 4,721,096; which is a continuation of Ser. No. 06/853,569, filed Apr. 18, 1986, now abandoned, each of which is incorporated by reference herein in its entirety.

TABLE OF CONTENTS
1. INTRODUCTION
2. BACKGROUND OF THE INVENTION
   2.1. LONG TERM CELL CULTURE
   2.2. CORRECTION OF DEFECTS IN THE BODY
3. SUMMARY OF THE INVENTION
   3.1. DEFINITIONS AND ABBREVIATIONS
4. DESCRIPTION OF THE FIGURES
5. DETAILED DESCRIPTION OF THE INVENTION: THE THREE-DIMENSIONAL CELL CULTURE SYSTEM
   5.1. ESTABLISHMENT OF THREE-DIMENSIONAL STROMAL TISSUE
   5.2. INOCULATION OF TISSUE-SPECIFIC CELLS ONTO THREE-DIMENSIONAL STROMAL MATRIX AND MAINTENANCE OF CULTURES
   5.3. USES OF THE TRANSPLANTABLE TISSUE GRAFTS GROWN IN THREE-DIMENSIONAL CULTURE SYSTEM
      5.3.1. TRANSPLANTATION IN VIVO
      5.3.2. SCREENING EFFECTIVENESS AND CYTOTOXICITY OF COMPOUNDS IN VITRO
      5.3.3. GENE THERAPY
6. TUBULAR BIOLOGICAL TISSUES
   6.1. SINGLE MESH LAYER TUBES
      6.1.1.. FLAT MESH STARTING MATERIAL
      6.1.2. TUBULAR MESH STARTING MATERIAL
   6.2. MULTIPLE MESH LAYERS TUBES
      6.2.1. MULTIPLE FLAT MESHES
      6.2.2. FLAT MESHES WRAPPED AROUND TUBULAR MESHES
      6.2.3. MULTIPLE TUBULAR MESHES
7. BLOOD VESSELS
   7.1. ARTERIES
   7.2. VEINS
8. GASTROINTESTINAL TRACT
9. GENITOURINARY TRACT
   9.1. URETER
   9.2. URETHRA
10. HERNIA REPAIR
11. FORMATION OF TENDONS AND LIGAMENTS

1. INTRODUCTION

The present invention relates to a stromal cell-based three-dimensional cell and tissue culture system and its use to form corrective structures that can be implanted and utilized in vivo. This culture system can be used for the long term proliferation of cells and tissues in vitro in an environment that more closely approximates that found in vivo. The culture system described herein provides for proliferation and appropriate cell maturation to form structures analogous to tissue counterparts in vivo. In particular, the invention relates to the use of the fibroblast-based three-dimensional cell culture system to construct complex structures such as, but not limited to, tubular sections of gastrointestinal and genitourinary tracts, blood vessels, tissues for hernia repair, tendons and ligaments. The three-dimensional cultures can be implanted in vivo to correct defects in the body.

2. BACKGROUND OF THE INVENTION

Cell culture systems have been used to study cells, expand cell populations for additional study, and in the production of recombinant gene products. However, cell culture systems have not been utilized for the repair of defects or abnormal tissues in the body.

2.1. Long Term Cell Culture

The majority of vertebrate cell cultures in vitro are grown as monolayers on an artificial substrate bathed in nutrient medium. The nature of the substrate on which the monolayers grow may be solid, such as plastic, or semisolid gels, such as collagen or agar. Disposable plastics have become the preferred substrate used in modern-day tissue or cell culture.

Some attempts have been made to use natural substrates related to basement membrane components. Basement membranes comprise a mixture of proteins, glycoproteins and proteoglycans that surround most cells in vivo. For example, Reid and Rojkund (1979, In, Methods in Enzymology, Vol. 57, Cell Culture, Jakoby & Pasten, eds., New York, Acad. Press, pp.263–278); Vlodavsky et al., (1980, Cell 19:607–617); Yang et al., (1979, Proc. Natl. Acad. Sci. U.S.A. 76:3401) have used collagen for culturing hepatocytes, epithelial cells and endothelial tissue. Growth of cells on floating collagen (Michalopoulos and Pitot, 1975, Fed. Proc. 34:826) and cellulose nitrate membranes (Savage and Bonney, 1978, Exp. Cell Res. 114:307–315) have been used in attempts to promote terminal differentiation. However, prolonged cellular regeneration and the culture of such tissues in such systems has not heretofore been achieved.

Cultures of mouse embryo fibroblasts have been used to enhance growth of cells, particularly at low densities. This effect is thought to be due partly to supplementation of the medium but may also be due to conditioning of the substrate by cell products. In these systems, feeder layers of fibroblasts are grown as confluent monolayers which make the surface suitable for attachment of other cells. For example, the growth of glioma on confluent feeder layers of normal fetal intestine has been reported (Lindsay, 1979, Nature 228:80).

While the growth of cells in two dimensions is a convenient method for preparing, observing and studying cells in culture, allowing a high rate of cell proliferation, it lacks the cell-cell and cell-matrix interactions characteristic of whole tissue in vivo. In order to study such functional and morphological interactions, a few investigators have explored the use of three-dimensional substrates such as collagen gel (Douglas et al., 1980, In Vitro 16:306–312; Yang et al., 1979, Proc. Natl. Acad. Sci. 76:3401; Yang et al., 1980, Proc. Natl. Acad. Sci. 77:2088–2092; Yang et al., 1981, Cancer Res. 41:1021–1027); cellulose sponge alone (Leighton et al., 1951, J. Natl. Cancer Inst. 12:545–561) or collagen coated (Leighton et al., 1968, Cancer Res. 28:286–296); a gelatin sponge, Gelfoam (Sorour et al., 1975, J. Neurosurg. 43:742–749).

In general, these three-dimensional substrates are inoculated with the cells to be cultured. Many of the cell types have been reported to penetrate the matrix and establish a "tissue-like" histology. For example, three-dimensional collagen gels have been utilized to culture breast epithelium (Yang et al., 1981, Cancer Res. 41:1021–1027) and sympathetic neurons (Ebendal, 1976, Exp. Cell Res. 98:159–169). Additionally, various attempts have been made to regenerate tissue-like architecture from dispersed monolayer cultures. Kruse and Miedema (1965, J. Cell Biol. 27:273) reported that perfused monolayers could grow to more than ten cells deep and organoid structures can develop in multilayered cultures if kept supplied with appropriate medium (see also Schneider et al., 1963, Exp. Cell Res. 30:449–459 and Bell et al., 1979, Proc. Natl. Acad. Sci. U.S.A. 76:1274–1279); Green (1978, Science 200:1385–1388) has reported that human epidermal keratinocytes may form dematoglyphs (friction ridges) if kept for several weeks without transfer; Folkman and Haudenschild (1980, Nature 288:551–556) reported the formation of capillary tubules in cultures of vascular endothelial cells cultured in the presence of endothelial growth factor and medium conditioned by tumor cells; and Sirica et al. (1979, Proc. Natl. Acad. Sci U.S.A. 76:283–287; 1980, Cancer Res. 40:3259–3267) maintained hepatocytes in primary culture for about 10–13 days on nylon meshes coated with a thin layer of collagen. However, the long term culture and proliferation of cells in such systems has not been achieved.

Indeed, the establishment of long term culture of tissues such as bone marrow has been attempted. Overall the results were disappointing, in that although a stromal cell layer containing different cell types is rapidly formed, significant hematopoiesis could not be maintained for any real time. (For review see Dexter et al., In Long Term Bone Marrow Culture,1984, Alan R. Liss, Inc., pp. 57–96).

2.2. Correction of Defects in the Body

Surgical approaches to correcting defects in the body, in general, involve the implantation of structures made of biocompatible, inert materials, that attempt to replace or substitute for the defective function. Non-biodegradable materials will result in permanent structures that remain in the body as a foreign object. Implants that are made of resorbable materials are suggested for use as temporary replacements where the object is to allow the healing process to replace the resorbed material. However, these approaches have met with limited success for the long-term correction of structures in the body. For example, the use of a tubular mesh as a surgical corrective device is described in U.S. Pat. No. 4,347,847 of F. C. Usher issued Sep. 7, 1982. This mesh was used neither to generate a specific tissue culture, nor to reconstruct a tubular structure. Rather it was sutured in place in a flattened configuration to join connective tissues together. In U.S. Pat. No. 4,520,821, issued Jun. 4, 1985, Schmidt et al. disclose the use of a tubular mesh to correct defects in the tubular structures of the genitourinary tract.

The foreign meshes could not fully replace the damaged tissue, since smooth muscle does not grow at the treated site. Bell included a smooth muscle cell layer in his attempt at constructing blood vessels described in U.S. Pat. No. 4,546, 500, issued Oct. 15, 1985. This construction, however, completely lacked elastin, a necessary component of blood vessels, and relied on a plastic mesh sleeve to provide the strength and elasticity required of blood vessels in vivo, with disappointing results. Thus, there has remained a need to construct tubular tissue structures (or constructs) such that they contain the cellular and extracellular components required to carry out the functions of their natural counterparts.

3. SUMMARY OF THE INVENTION

The present invention relates to a stromal cell-based three-dimensional cell culture system which can be used to culture a variety of different cells and tissues in vitro for prolonged periods of time. Growth of stromal cells on the three-dimensional framework results in the formation of a three-dimensional living stromal tissue which can be utilized in the body as a corrective structure. For example, and not by way of limitation, the three-dimensional cultures can be used to form tubular structures, like those of the gastrointestinal and genitourinary tracts, as well as blood vessels; tissues for hernia repair; tendons and ligaments; etc.

In accordance with the invention, stromal cells, such as fibroblasts, are inoculated and grown on a three-dimensional framework. The framework may be configured into the shape of the corrective structure desired. Stromal cells may also include other cells found in loose connective tissue such as smooth muscle cells, endothelial cells, macrophages/monocytes, adipocytes, pericytes, reticular cells found in bone marrow stroma, chondrocytes, etc. During growth in vitro the stromal cells deposit their extracellular matrix proteins onto the framework, thus forming a living stromal tissue; i.e., the stromal cells and connective tissue proteins naturally secreted by the stromal cells attach to and substantially envelope the framework composed of a biocompatible non-living material formed into a three-dimensional structure having interstitial spaces bridged by the stromal cells. The living stromal tissue so formed provides the support, growth factors, and regulatory factors necessary to sustain long-term active proliferation of cells in culture and deposition of appropriate matrix proteins. When grown in this three-dimensional system, the proliferating cells mature and segregate properly to form components of adult tissues analogous to counterparts found in vivo.

The invention is based, in part, on the discovery that growth of stromal cells in three dimensions will sustain active proliferation of cells in culture for longer periods of time than will monolayer systems. This may be due, in part, to the increased surface area of the three-dimensional framework which results in a prolonged period of active proliferation of stromal cells. These proliferating stromal cells elaborate proteins, growth factors and regulatory factors necessary to support the long term proliferation of both stromal and tissue-specific cells inoculated onto the stromal matrix. In addition, the three-dimensionality of the matrix allows for a spatial distribution which more closely approximates conditions in vivo, thus allowing for the formation of microenvironments conducive to cellular maturation and migration. The growth of cells in the presence of this support may be further enhanced by adding proteins, glycoproteins, glycosaminoglycans, a cellular matrix, and other materials to support itself or by coating the support with these materials. The three-dimensional framework can be shaped to assume the conformation of natural organs and their components.

In another embodiment of the invention, the stromal cells can be genetically engineered to express a gene product beneficial for successful and/or improved transplantation. For example, in the case of vascular grafts, the stromal cells can be genetically engineered to express anticoagulation gene products to reduce the risk of thromboembolism, atherosclerosis, occlusion, or anti-inflammatory gene products to reduce risk of failure. For example, the stromal cells can be genetically engineered to express tissue plasminogen activator (TPA), streptokinase or urokinase to reduce the risk of clotting. Alternatively, the stromal cells can be engineered to express anti-inflammatory gene products, e.g., peptides or polypeptides corresponding to the idiotype of neutralizing antibodies for tumor necrosis factor (TNF), interleukin-2 (IL-2), or other inflammatory cytokines. Preferably, the cells are engineered to express such gene products transiently and/or under inducible control during the post-operative recovery period, or as a chimeric fusion protein anchored to the stromal cell, e.g., a chimeric molecule composed of an intracellular and/or transmembrane domain of a receptor or receptor-like molecule, fused to the gene product as the extracellular domain.

In another alternative, the stromal cells can be genetically engineered to "knock out" expression of factors or surface antigens that promote clotting or rejection. For example, expression of fibrinogen, von Willebrands factor or any cell surface molecule that binds to the platelet α2Bβ-3 receptor can be knocked out in the stromal cells to reduce the risk of clot formation. Likewise, the expression of MHC class II molecules can be knocked out in order to reduce the risk of rejection of the graft.

In yet another embodiment of the invention, the three-dimensional culture system of the invention may afford a vehicle for introducing genes and gene products in vivo to assist or improve the results of the transplantation and/or for use in gene therapies. For example, genes that prevent or ameliorate symptoms of vascular disease such as thrombus formation, atherosclerosis, inflammatory reactions, fibrosis and calcification, may be underexpressed or overexpressed in disease conditions. Thus, the level of gene activity in the patient may be increased or decreased, respectively, by gene replacement therapy by adjusting the level of the active gene product in genetically engineered stromal cells.

In another alternative, the stromal cells can be genetically engineered to block gene expression necessary for the transition of smooth muscle cells to proliferate, migrate and to lead to development of neointimal hyperplasia, e.g., by antisense oligodeoxynucleotide blockade of expression of cell division cycle 2 kinase and proliferating cell nuclear antigen. Mann, M. J., et al., 1995, Proc. Natl. Acad. Sci. U.S.A. 92:4502–4506.

The present invention relates to methods and biological tissue, tubular sections or constructs for the treatment, reconstruction and/or replacement of defects in the body, including, but not limited to, gastrointestinal and genitourinary tracts, blood vessels such as arteries and veins, tissues for hernia repair, tendons and ligaments.

3.1. Definitions and Abbreviations

The following terms used herein shall have the meanings indicated:

Adherent Layer: cells attached directly to the three-dimensional support or connected indirectly by attachment to cells that are themselves attached directly to the support.

Stromal Cells: fibroblasts with or without other cells and/or elements found in loose connective tissue, including but not limited to, endothelial cells, pericytes, macrophages, monocytes, plasma cells, mast cells, adipocytes, etc.

Tissue-Specific or Parenchymal Cells: the cells which form the essential and distinctive tissue of an organ as distinguished from its supportive framework.

Three-Dimensional Framework: a three-dimensional scaffold composed of any material and/or shape that (a) allows cells to attach to it (or can be modified to allow cells to attach to it); and (b) allows cells to grow in more than one layer. This support is inoculated with stromal cells to form the living three-dimensional stromal tissue.

Three-Dimensional Stromal Tissue: a three-dimensional framework which has been inoculated with stromal cells that are grown on the support. The extracellular matrix proteins elaborated by the stromal cells are deposited onto the framework, thus forming a living stromal tissue. The living stromal tissue can support the growth of tissue-specific cells later inoculated to form the three-dimensional cell culture.

Three-Dimensional Cell Culture: a three-dimensional living stromal tissue which has been inoculated with tissue-specific cells and cultured. In general, the tissue specific cells used to inoculate the three-dimensional stromal matrix should include the "stem" cells (or "reserve" cells) for that tissue; i.e., those cells which generate new cells that will mature into the specialized cells that form the parenchyma of the tissue.

The following abbreviations shall have the meanings indicated:

BFU-E=burst-forming unit-erythroid
CFU-C=colony forming unit-culture
CFU-GEMM=colony forming unit-granuloid, erythroid, monocyte, megakaryocyte
EDTA=ethylene diamine tetraacetic acid
FBS=fetal bovine serum
HBSS=Hank's balanced salt solution
HS=horse serum
LTBMC=long term bone marrow culture
MEM=minimal essential medium
PBL=peripheral blood leukocytes
PBS=phosphate buffered saline
RPMI 1640=Roswell Park Memorial Institute medium number 1640 (GIBCO, Inc., Grand Island, N.Y.)
SEM=scanning electron microscopy

4. DESCRIPTION OF THE FIGURES

FIG. 1 is a scanning electron micrograph depicting attachment to the three-dimensional matrix and extension of cellular processes across the mesh opening. Fibroblasts are actively secreting matrix proteins and are at the appropriate stage of subconfluency which should be obtained prior to inoculant with tissue-specific cells.

5. DETAILED DESCRIPTION OF THE INVENTION: THE THREE-DIMENSIONAL CELL CULTURE SYSTEM

The present invention relates to three-dimensional living stromal tissues that can be used as corrective structures in the body, including, but not limited to, tubular structures that can be used to replace or repair blood vessels, gastrointestinal tract, or urinary tract; filamentous or tubular structures that can be used to replace or repair tendons and ligaments; and tubular or flat structures that can be used to repair defects such as hernias. The living stromal tissue of the invention comprises stromal cells grown on a three-dimensional framework, matrix or network. The three-dimensional framework can be formed into any desired shape; e.g., mesh type frameworks can be used to form tubular structures; rope-like structures can be woven or tubes or filaments can be used as the framework for growing tendons and ligaments, etc.

In previously known tissue culture systems, the cells were grown in a monolayer. Cells grown on a three-dimensional stromal support, in accordance with the present invention, grow in multiple layers, forming a cellular matrix. This matrix system approaches physiologic conditions found in vivo to a greater degree than previously described monolayer tissue culture systems. The three-dimensional cell culture system is applicable to the proliferation of different types of cells and formation of a number of different tissues, including but not limited to bone marrow, skin, liver, pancreas, kidney, adrenal and neurologic tissue, as well as tissues of the gastrointestinal and genitourinary tracts, and the circulatory system, to name but a few. See U.S. Pat. Nos. 4,721,096; 4,963,489; 5,032,508; 5,266,480; and 5,160,490, each of which is incorporated by reference herein in its entirety.

The stromal cells used in the three-dimensional cultures comprise fibroblasts with or without additional cells and/or elements described more fully herein. The fibroblasts and other cells and/or elements that comprise the stroma may be fetal or adult in origin, and may be derived from convenient sources such as skin, liver, pancreas, arteries, veins, umbilical cord, and placental tissues, etc. Such tissues and/or organs can be obtained by appropriate biopsy or upon autopsy. In fact, cadaver organs may be used to provide a generous supply of stromal cells and elements.

Fetal fibroblasts will support the growth of many different cells and tissues in the three-dimensional culture system, and, therefore, can be inoculated onto the matrix to form a "generic" stromal support matrix for culturing any of a variety of cells and tissues. However, in certain instances, it may be preferable to use a "specific" rather than "generic" stromal support matrix, in which case stromal cells and elements can be obtained from a particular tissue, organ, or individual. For example, where the three-dimensional culture is to be used for purposes of transplantation or implantation in vivo, it may be preferable to obtain the stromal cells and elements from the individual who is to receive the transplant or implant. This approach might be especially advantageous where immunological rejection of the transplant and/or graft versus host disease is likely. Moreover, fibroblasts and other stromal cells and/or elements may be derived from the same type of tissue to be cultured in the three-dimensional system. This might be advantageous when culturing tissues in which specialized stromal cells may play particular structural/functional roles; e.g., smooth muscle cells of arteries, glial cells of neurological tissue, Kupffer cells of liver, etc.

Once inoculated onto the three-dimensional support, the stromal cells will proliferate on the framework and deposit the connective tissue proteins naturally secreted by the stromal cells. The stromal cells and their naturally secreted connective tissue proteins substantially envelop the framework thus forming the living stromal tissue which will support the growth of tissue-specific cells inoculated into the three-dimensional culture system of the invention. In fact, when inoculated with the tissue-specific cells, the three-dimensional stromal tissue will sustain active proliferation of the culture for long periods of time. Importantly, because openings in the mesh permit the exit of stromal cells in culture, confluent stromal cultures do not exhibit contact inhibition, and the stromal cells continue to grow, divide, and remain functionally active.

Growth and regulatory factors may be added to the culture, but are not necessary since they are elaborated by the stromal tissue. The use of growth factors (for example, but not limited to, αFGF, βFGF, insulin growth factor or TGF-betas), or natural or modified blood products or other bioactive biological molecules (for example, but not limited to, hyaluronic acid or hormones), even though not absolutely necessary in the present invention, may be used to further enhance the colonization of the three-dimensional framework or scaffolding.

Because, according to the invention, it is important to recreate, in culture, the cellular microenvironment found in vivo for a particular tissue, the extent to which the stromal cells are grown prior to use of the cultures in vivo may vary depending on the type of tissue to be grown in three-dimensional tissue culture. The living stromal tissues may be used as corrective structures by implanting them in vivo. Alternatively, the living stromal tissues may be inoculated with another cell type and implanted in vivo, with or without prior culturing in vitro. In addition, the stromal cells grown in the system may be genetically engineered to produce gene products beneficial to transplantation, e.g., anti-inflammatory factors, e.g., anti-GM-CSF, anti-TNF, anti-IL-1, anti-IL-2, etc. Alternatively, the stromal cells may be genetically engineered to "knock out" expression of native gene products that promote inflammation, e.g., GM-CSF, TNF, IL-1, IL-2, or "knock out" expression of MHC in order to lower the risk of rejection. In addition, the stromal cells may be genetically engineered for use in gene therapy to adjust the level of gene activity in a patient to assist or improve the results of the tubular tissue transplantation.

In another alternative, the stromal cells can be genetically engineered to block gene expression necessary for the transition of smooth muscle cells to proliferate, migrate and to lead to development of neointimal hyperplasia, e.g., by antisense oligodeoxynucleotide blockade of expression of cell division cycle 2 kinase and proliferating cell nuclear antigen.

The invention is based, in part, upon the discovery that growth of the stromal cells in three dimensions will sustain active proliferation of both the stromal and tissue-specific cells in culture for much longer time periods than will monolayer systems. Moreover, the three-dimensional system supports the maturation, differentiation, and segregation of cells in culture in vitro to form components of adult tissues analogous to counterparts found in vivo.

In yet another application, the three-dimensional tubular tissue or construct may be grown within a "bioreactor" to produce grafts populated with viable human cells. For example, but not limited to, a vascular graft, which may be assembled as a three-dimensional framework and housed in the treatment chamber of the bioreactor. Applying radial stress to the vascular graft located in the treatment chamber during seeding and culturing results in a vascular graft with cells and their fibers oriented so as to more likely tolerate the physiological conditions found in the human body. In this manner, the "bioreactor" creates a dynamic environment in which to seed and culture tissue-engineered vascular or other biological grafts or other implantable constructs.

Although the applicants are under no duty or obligation to explain the mechanism by which the invention works, a number of factors inherent in the three-dimensional culture system may contribute to its success:

(a) The three-dimensional framework provides a greater surface area for protein attachment, and consequently, for the adherence of stromal cells; and (b) Because of the three-dimensionality of the framework, stromal cells continue to grow actively, in contrast to cells in monolayer cultures, which grow to confluence, exhibit contact inhibition,.and cease to grow and divide. The elaboration of growth and regulatory factors by replicating stromal cells may be partially responsible for stimulating proliferation and regulating differentiation of cells in culture;

(c) The three-dimensional framework allows for a spatial distribution of cellular elements which is more analogous to that found in the counterpart tissue in vivo;

(d) The increase in potential volume for cell growth in the three-dimensional system may allow the establishment of localized microenvironments conducive to cellular maturation;

(e) The three-dimensional framework maximizes cell-cell interactions by allowing greater potential for movement of migratory cells, such as macrophages, monocytes and possibly lymphocytes in the adherent layer;

(f) It has been recognized that maintenance of a differentiated cellular phenotype requires not only growth/ differentiation factors but also the appropriate cellular interactions. The present invention effectively recreates the tissue microenvironment.

The three-dimensional stromal tissues, the culture system itself, and its maintenance, as well as various uses of the three-dimensional cultures are described in greater detail in the subsections below.

5.1. Establishment of Three-Dimensional Stromal Tissue

The three-dimensional support or framework may be of any material and/or shape that: (a) allows cells to attach to it-(or can be modified to allow cells to attach to it); and (b) allows cells to grow in more than one layer. A number of different materials may be used to form the framework, including but not limited to: non-biodegradable materials, e.g., nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton; and biodegradable materials, e.g., polyglycolic acid (PGA), collagen, collagen sponges, cat gut sutures, cellulose, gelatin, dextran, polyalkanoates, etc. Any of these materials may be woven braided, knitted, etc., into a mesh, for example, to form the three-dimensional framework. The framework, in turn can be fashioned into any shape desired as the corrective structure, e.g., tubes, ropes, filaments, etc. Certain materials, such as nylon, polystyrene, etc., are poor substrates for cellular attachment. When these materials are used as the three-dimensional framework, it is advisable to pre-treat the framework prior to inoculation of stromal cells in order to enhance the attachment of stromal cells to the support. For example, prior to inoculation with stromal cells, nylon frameworks could be treated with 0.1M acetic acid, and incubated in polylysine, FBS, and/or collagen to coat the nylon. Polystyrene could be similarly treated using sulfuric acid.

For implantation of the three-dimensional culture in vivo, it may be preferable to use biodegradable matrices such as polyglycolic acid, collagen, collagen sponges, woven collagen, catgut suture material, gelatin, polylactic acid, or polyglycolic acid and copolymers thereof, for example. Where the cultures are to be maintained for long periods of time or cryopreserved, non-degradable materials such as nylon, dacron, polystyrene, polyacrylates, polyvinyls, teflons, cotton, etc., may be preferred. A convenient nylon mesh which could be used in accordance with the invention is Nitex, a nylon filtration mesh having an average pore size of 210 $\mu$m and an average nylon fiber diameter of 90 $\mu$m (#3-210/36, Tetko, Inc., New York).

Stromal cells comprising fibroblasts, with or without other cells and elements described below, are inoculated onto the framework. These fibroblasts may be derived from organs, such as skin, liver, pancreas, etc., which can be obtained by biopsy (where appropriate) or upon autopsy. In fact fibroblasts can be obtained in quantity rather conveniently from any appropriate cadaver organ. As previously explained, fetal fibroblasts can be used to form a "generic" three-dimensional stromal matrix that will support the growth of a variety of different cells and/or tissues. However, a "specific" stromal tissue may be prepared by inoculating the three-dimensional framework with fibroblasts derived from the same type of tissue to be cultured and/or from a particular individual who is later to receive the cells and/or tissues grown in culture in accordance with the three-dimensional system of the invention.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137–168.

The isolation of fibroblasts may, for example, be carried out as follows: fresh tissue samples are thoroughly washed and minced an Hanks balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional matrix (see, Naughton et al., 1987, J. Med. 18 (3 and 4) 219–250). Inoculation of the three-dimensional framework with a high concentration of stromal cells, e.g., approximately $10^6$ to $5 \times 10^7$ cells/ml, will result in the establishment of the three-dimensional stromal tissue in shorter periods of time.

In addition to fibroblasts, other cells may be added to form the three-dimensional stromal tissue. For example, other cells found in loose connective tissue may be inoculated onto the three-dimensional support along with fibroblasts. Such cells include but are not limited to smooth muscle cells, endothelial cells, pericytes, macrophages, monocytes, plasma cells, mast cells, adipocytes, etc. These stromal cells may readily be derived from appropriate organs such as arteries, skin, liver, etc., using methods known in the art such as those discussed above. In one embodiment of the invention, stromal cells which are specialized for the particular tissue to be cultured may be added to the fibroblast stroma. For example, stromal cells of hematopoietic tissue, including but not limited to fibroblasts, endothelial cells, macrophages/monocytes, adipocytes and reticular cells, could be used to form the three-dimensional subconfluent stroma for the long term culture of bone marrow in vitro. Hematopoietic stromal cells may be readily obtained from the "buffy coat" formed in bone marrow suspensions by centrifugation at low forces, e.g., 3000×g. In the stromal layer that makes up the inner wall of arteries, a high proportion of undifferentiated smooth muscle cells can be added to provide the protein elastin. Stromal cells of liver may include fibroblasts, Kupffer cells, and vascular and bile duct endothelial cells. Similarly, glial cells could be used as the stroma to support the proliferation of neurological cells and tissues; glial cells for this purpose can be obtained by trypsinization or collagenase digestion of embryonic or adult brian (Ponten and Westermark, 1980, in Federof, S. Hertz, L., eds, "Advances in Cellular Neurobiology," Vol. 1, New York, Academic Press, pp. 209–227). Again, where the cultured cells are to be used for transplantation or implantation in vivo it is preferable to obtain the stromal cells from the patient's own tissues. The growth of cells in the three-dimensional stromal cell culture may be further enhanced by adding to the framework, or coating the support with proteins (e.g., collagens, elastic fibers, reticular fibers) glycoproteins, glycosaminoglycans (e.g., heparan sulfate, chondroitin-4-sulfate, chondroitin-6-sulfate, dermatan sulfate, keratin sulfate, etc.), a cellular matrix, and/or other materials.

The stromal cells may be inoculated onto the framework before or after forming the shape desired for implantation, e.g., tubes, ropes, filaments. After inoculation of the stromal cells, the three-dimensional framework should be incubated in an appropriate nutrient medium. Many commercially available media such as RPMI 1640, Fisher's, Iscove's, McCoy's, and the like may be suitable for use. It is important that the three-dimensional stromal cell cultures be suspended or floated in the medium during the incubation period in order to maximize proliferative activity. In addition, the culture should be "fed" periodically to remove the spent media, depopulate released cells, and add fresh media.

During the incubation period, the stromal cells will grow linearly along and envelop the three-dimensional framework before beginning to grow into the openings of the framework. It is important to grow the cells to an appropriate degree which reflects the amount of stromal cells present in the in vivo tissue prior to inoculation of the stromal matrix with the tissue-specific cells.

The openings of the framework should be of an appropriate size to allow the stromal cells to stretch across the openings. Maintaining actively growing stromal cells which stretch across the framework enhances the production of growth factors which are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of support, as exemplified herein, we have found that openings ranging from about 150 $\mu$m to about 220 $\mu$m will work satisfactorily. However, depending upon the three-dimensional structure and intricacy of the framework, other sizes may work equally well. In fact, any shape or structure that allow the stromal cells to stretch and continue to replicate and grow for lengthy time periods will work in accordance with the invention.

Different proportions of the various types of collagen deposited on the support can also affect the growth of tissue-specific or other cells which may be later inoculated onto the stromal tissue or which may grow onto the structure in vivo. For example, for optimal growth of hematopoietic cells, the matrix should preferably contain collagen types III, IV and I in an approximate ratio of 6:3:1 in the initial matrix. For three-dimensional skin culture systems, collagen types I and III are preferably deposited in the initial matrix. The proportions of collagen types deposited can be manipulated or enhanced by selecting stromal cells which elaborate the appropriate collagen type and inoculating such stromal cells onto the framework. For example, fibroblasts can be selected using monoclonal antibodies of an appropriate isotype or subclass that is capable of activating complement, and which define particular collagen types. These antibodies and complement can be used to select negatively the fibroblasts which express the desired collagen type. Alternatively, the stroma used to inoculate the matrix can be a mixture of cells which synthesize the appropriate collagen types desired. The distribution and origins of the five types of collagen is shown in Table I.

TABLE I

DISTRIBUTIONS AND ORIGINS OF THE FIVE TYPES OF COLLAGEN

| Collagen Type | Principal Tissue Distribution | Cells of Origin |
|---|---|---|
| I | Loose and dense ordinary connective tissue; collagen fibers Fibrocartilage Bone Dentin | Fibroblasts and reticular cells; smooth muscle cells Osteoblast Odontoblasts |
| II | Hyaline and elastic cartilage Vitreous body of eye | Chondrocytes Retinal cells |
| III | Loose connective tissue; reticular fibers Papillary layer of dermis Blood vessels | Fibroblasts and reticular cells Smooth muscle cells; endothelial cells |
| IV | Basement membranes Lens capsule of eye | Epithelial and endothelial cells Lens fibers |
| V | Fetal membranes; placenta Basement membranes | Fibroblasts |

TABLE I-continued

DISTRIBUTIONS AND ORIGINS OF THE FIVE
TYPES OF COLLAGEN

| Collagen Type | Principal Tissue Distribution | Cells of Origin |
|---|---|---|
| | Bone Smooth muscle | Smooth muscle cells |

Thus, depending upon the tissue to be cultured and the collagen types desired, the appropriate stromal cell(s) may be selected to inoculate the three-dimensional matrix.

Similarly, the relative amounts of collagenic and elastic fibers present in the stromal layer can be modulated by controlling the ratio of collagen producing cells to elastin producing cells in the initial inoculum. For example, since the inner walls of arteries are rich in elastin, an arterial stroma should contain a high concentration of the undifferentiated smooth muscle cells which elaborate elastin.

During incubation of the three-dimensional stromal cell cultures, proliferating cells may be released from the matrix. These released cells may stick to the walls of the culture vessel where they may continue to proliferate and form a confluent monolayer. This should be prevented or minimized, for example, by removal of the released cells during feeding, or by transferring the three-dimensional stromal culture to a new culture vessel. The presence of a confluent monolayer in the vessel will "shut down" the growth of cells in the three-dimensional matrix and/or culture. Removal of the confluent monolayer or transfer of the culture to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the culture, so that they will not stick to the walls of the vessel and grow to confluence. In any case, the released stromal cells can be collected and cryopreserved for future use.

The living stromal tissue so formed can be used as a corrective structure in vivo. Alternatively, other cells, such as parenchymal cells, may be inoculated and grown on the three-dimensional living stromal tissue prior to implantation in vivo.

5.2. Inocullation of Tissue-Specific Cells onto Three-Dimensional Stromal Matrix and Maintenance of Cultures Once the three-dimensional stromal cell culture has reached the appropriate degree of growth, additional cells such as tissue-specific cells (parenchymal cells) or surface layer cells which are desired to be cultured may also be inoculated onto the living stromal tissue. Such cells inoculated onto the living stromal tissue can be incubated to allow the cells to adhere to the stromal tissue, and implanted in vivo where continued growth can occur. Alternatively, the cells can be grown on the living stromal tissue in vitro to form a cultured counterpart of the native tissue prior to implantation in vivo. A high concentration of cells in the inoculum will advantageously result in increased proliferation in culture much sooner than will low concentrations. The cells chosen for inoculation will depend upon the tissue to be cultured, which may include, but is not limited to, bone marrow, skin, liver, pancreas, kidney, neurological tissue, adrenal gland, mucosal epithelium, endothelium, and smooth muscle, to name but a few.

For example, and not by way of limitation, a variety of epithelial cells can be cultured on the three-dimensional living stromal tissue. Examples of such epithelial cells include, but are not limited to, oral mucosa and gastrointestinal (G.I.) tract cells. Such epithelial cells may be isolated by enzymatic treatment of the tissue according to methods known in the art, followed by expansion of these cells in culture and application of epithelial cells to the three-dimensional stromal support cell matrix (neo-submucosa). The presence of the submucosa provides growth factors and other proteins which promote normal division and differentiation of themoral mucosa cells and the cells of the G.I. tract lining. Using this methodology, other epithelial cells can be grown successfully, including nasal epithelium, respiratory tract epithelium, vaginal epithelium, and corneal epithelium.

In general, this inoculum should include the "stem" cell (also called the "reserve" cell) for that tissue; i.e., those cells which generate new cells that will mature into the specialized cells that form the various components of the tissue.

The parenchymal or other surface layer cells used in the inoculum may be obtained from cell suspensions prepared by disaggregating the desired tissue using standard techniques described for obtaining stromal cells in Section 5.1 above. The entire cellular suspension itself could be used to inoculate the three-dimensional living stromal tissue. As a result, the regenerative cells contained within the homogenate will proliferate, mature, and differentiate properly on the matrix, whereas non-regenerative cells will not. Alternatively, particular cell types may be isolated from appropriate fractions of the cellular suspension using standard techniques described for fractionating stromal cells in Section 5.1 above. Where the "stem" cells or "reserve" cells can be readily isolated, these may be used to preferentially inoculate the three-dimensional stromal support. For example, when culturing bone marrow, the three-dimensional stroma may be inoculated with bone marrow cells, either fresh or derived from a cryopreserved sample. When culturing skin, the three-dimensional stroma may be inoculated with melanocytes and keratinocytes. When culturing liver, the three-dimensional stroma may be inoculated with hepatocytes. When culturing pancreas, the three-dimensional stroma may be inoculated with pancreatic endocrine cells. For a review of methods which may be utilized to obtain parenchymal cells from various tissues, see, Freshney, Culture of Animal Cells. A Manual of Basic Technique, 2d Ed., A. R. Liss, Inc., New York, 1987, Ch. 20, pp. 257–288.

During incubation, the three-dimensional cell culture system should be suspended or floated in the nutrient medium. Cultures should be fed with fresh media periodically. Again, care should be taken to prevent cells released from the culture from sticking to the walls of the vessel where they could proliferate and form a confluent monolayer. The release of cells from the three-dimensional culture appears to occur more readily when culturing diffuse tissues as opposed to structured tissues. For example, the three-dimensional skin culture of the invention is histologically and morphologically normal; the distinct dermal and epidermal layers do not release cells into the surrounding media. By contrast, the three-dimensional bone marrow cultures of the invention release mature non-adherent cells into the medium much the way such cells are released in marrow in vivo. As previously explained, should the released cells stick to the culture vessel and form a confluent monolayer, the proliferation of the three-dimensional culture will be "shut down". This can be avoided by removal of released cells during feeding, transfer of the three-dimensional culture to a new vessel, by agitation of the culture to prevent sticking of released cells to the vessel wall, or by the continuous flow of fresh media at a rate sufficient to replenish nutrients in the culture and remove released cells. In any case, the mature released cells could be collected and cryopreserved for future use.

Growth factors and regulatory factors need not be added to the media since these types of factors ate elaborated by the three-dimensional stromal cells. However, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

5.3. Uses of the Transplantable Tissue Grafts Grown in Three-Dimensional Culture System The three-dimensional culture system of the invention can be used in a variety of applications. These include but are not limited to transplantation or implantation of either the cultured cells obtained from the matrix, or the cultured matrix itself in vivo. The three-dimensional tissue culture implants may, according to the invention, be used to replace or augment existing tissue, to introduce new or altered tissue, to modify artificial prostheses, or to join together biological tissues or structures. For example, and not by way of limitation, specific embodiments of the invention include but are not limited to: (i) dental prostheses joined to a three-dimensional culture of oral mucosa; (ii) tubular three-dimensional tissue implants (such as gastrointestinal tract, genitourinary tract and blood vessels; (iii) ligament or tendon implants; (iv) tissues for hernia repair; and (v) genetically altered cells grown in the three-dimensional culture which express a recombinant gene product.

5.3.1. Transplantation in Vivo

The three-dimensional cultures can be implanted in vivo to correct defects; replace surgically removed tissues; repair joints; implant shunts; repair hernias; etc. To this end, the living stromal tissue itself could be implanted in vivo. Depending upon the application, the implant may first be treated to kill the cells in the culture prior to implantation. For example, when treating conditions where growth factors may aggravate a pre-existing condition, e.g., in rheumatoid arthritis, it may be preferred to kill the cells which produce growth factors in the culture. This can be accomplished after the stromal tissue is formed in vitro but prior to implantation in vivo, by irradiation, or by freeze-thawing the cultures and washing away components of lysed cells. Alternatively, where enhancement of wound healing is desired, the cultures can be implanted in a viable state so that growth factors are produced at the implant site. In yet another alternative, other cells, such as parenchymal cells, may be inoculated onto the living stromal tissue prior to implantation in vivo. These cultures may be further grown in vitro prior to implantation in vivo.

The basic manifestation of a hernia is a protrusion of the abdominal contents into a defect within the fascia. Surgical approaches toward hernia repair is focused on reducing the hernial contents into the peritoneal cavity and producing a firm closure of the fascial defect either by using prosthetic, allogeneic or autogenous materials. A number of techniques have been used to produce this closure including the movement of autologous tissues and the use of synthetic mesh products. Drawbacks to these current products and procedures include hernia recurrence, where the closure weakens again, allowing the abdominal contents back into the defect.

Insertion of the cultured invention in hernia repair would be likely via an open procedure despite trends toward minimally invasive surgeries as the conversion of herniorrhaphy from open to endoscopic procedures has proved slow.

In yet another example, ligaments and tendons are viscoelastic structures that increase in brittleness with age, leading to ligamentous tears. These structures are complex, relatively static collagenous structures with functional links to the bone, muscle, menisci and other nearby tendons and ligaments. Surgical repair of these structures are conducted via either open procedures or arthroscopically-assisted procedures. Autografts are typically used from other sites in the knee. However, autografts can cause donor site morbidity. Other materials which are used in place of autografts, such as allografts, bovine tendons, polyesters and carbon fiber reinforced polymers, are subject to mechanical failure and can cause immunogenic complications.

5.3.2. Screening Effectiveness and Cytotoxicity of Compounds in Vitro

The three-dimensional cultures may be used in vitro to screen a wide variety of compounds, for effectiveness and cytotoxicity of pharmaceutical agents, growth/regulatory factors, natural and modified blood products, anticoagulants, clotting agents or anti-calcification agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed.

5.3.3. Gene Therapy

The three-dimensional culture system of the invention may afford a vehicle for introducing genes and gene products in vivo to assist or improve the results of the transplantation and/or for use in gene therapies. For example, for vascular grafts, the stromal cells can be genetically engineered to express anticoagulation gene products to reduce the risk of thromboembolism, or anti-inflammatory gene products to reduce the risk of failure due to inflammatory reactions. In this regard, the stromal cells can be genetically engineered to express TPA, streptokinase or urokinase to reduce the risk of clotting. Alternatively, for vascular or other types of tissue grafts, the stromal cells can be engineered to express anti-inflammatory gene products, for example, peptides or polypeptides corresponding to the idiotype of neutralizing antibodies for TNF, IL-2, or other inflammatory cytokines. Preferably, the cells are engineered to express such gene products transiently and/or under inducible control during the post-operative recovery period, or as a chimeric fusion protein anchored to the stromal cells, for example, a chimeric molecule composed of an intracellular and/or transmembrane domain of a receptor or receptor-like molecule, fused to the gene product as the extracellular domain. In another embodiment, the stromal cells could be genetically engineered to express a gene for which a patient is deficient, or which would exert a therapeutic effect, e.g., HDL, apolipoprotein E, etc. The genes of interest engineered into the stromal cells need to be related to the disease being treated. For example, for vascular disease the stromal cells can be engineered to express gene products that are carried by the blood; e.g., cerebredase, adenosine deaminase, α-1-antitrypsin. In a particular embodiment, a genetically engineered vascular graft culture implanted to replace a section of a vein or artery can be used to deliver gene products such as α-1-antitrypsin to the lungs; in such an approach, constitutive expression of the gene product is preferred.

The stromal cells can be engineered using a recombinant DNA construct containing the gene used to transform or transfect a host cell which is cloned and then clonally expanded in the three-dimensional culture system. The three-dimensional culture which expresses the active gene product, could be implanted into an individual who is deficient for that product. For example, genes that prevent or ameliorate symptoms of various types of vascular, genitourinary tract, hernia or gastrointestinal diseases may be underexpressed or down regulated under disease conditions. Specifically, expression of genes involved in preventing the following pathological conditions may be down-regulated, for example: thrombus formation, inflammatory reactions, and fibrosis and calcification of the valves. Alternatively, the activity of gene products may be diminished, leading to the manifestations of some or all of the above pathological conditions and eventual development of symptoms of valvular disease. Thus, the level of gene activity may be increased by either increasing the level of gene product present or by increasing the level of the active gene product which is present in the three-dimensional culture system. The three-dimensional culture which expresses the active target gene product can then be implanted into the valvular disease patient who is deficient for that product. "Target gene," as used herein, refers to a gene involved in diseases such as, but not limited to, vascular, genitourinary tract, hernia or gastrointestinal disease in a manner by which modulation of the level of target gene expression or of target gene product activity may act to ameliorate symptoms of valvular disease.

Further, patients may be treated by gene replacement therapy during the post-recovery period after transplantation. Tissue constructs or sheets may be designed specifically to meet the requirements of an individual patient, for example, the stromal cells may be genetically engineered to regulate one or more genes; or the regulation of gene expression may be transient or long-term; or the gene activity may be non-inducible or inducible. For example, one or more copies of a normal target gene, or a portion of the gene that directs the production of a normal target gene protein product with target gene function, may be inserted into human cells that populate the three-dimensional constructs using either non-inducible vectors including, but are not limited to, adenovirus, adeno-associated virus, and retrovirus vectors, or inducible promoters, including metallothionein, or heat shock protein, in addition to other particles that introduce DNA into cells, such as liposomes or direct DNA injection or in gold particles. For example, the gene encoding the human complement regulatory protein, which prevents rejection of the graft by the host, may be inserted into human fibroblasts. Nature 375:89 (May, 1995).

The three-dimensional cultures containing such genetically engineered stromal cells, e.g., either mixtures of stromal cells each expressing a different desired gene product, or a stromal cell engineered to express several specific genes are then implanted into the patient to allow for the amelioration of the symptoms of diseases such as, but not limited to, vascular, genitourinary tract, hernia or gastrointestinal disease. The gene expression may be under the control of a non-inducible (i.e., constitutive) or inducible promoter. The level of gene expression and the type of gene regulated can be controlled depending upon the treatment modality being followed for an individual patient.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells.

A variety of methods may be used to obtain the constitutive or transient expression of gene products engineered into the stromal cells. For example, the transkaryotic implantation technique described by Seldon, R. F., et al., 1987, Science 236:714–718 can be used. "Transkaryotic", as used herein, suggests that the nuclei of the implanted cells have been altered by the addition of DNA sequences by stable or transient transfection. The cells can be engineered using any of the variety of vectors including, but not limited to, integrating viral vectors, e.g., retrovirus vector or adeno-associated viral vectors, or non-integrating replicating vectors, e.g., papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter.

Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins (e.g., those characterized by abundant rough endoplasmic reticulum, and golgi complex) are preferable. Hosts cells can be transformed with DNA controlled by appropriate expression control elements (e.g., promoter, enhancer, sequences, transcription terminators, polyadenylation sites, etc.) and a selectable marker. Following the introduction of the foreign DNA, engineered cells may be allowed to grow in an enriched media, and then are switched to a selective media. The selectable marker in the recombinant plasmid confers resistance to the selection and allows cells to stably integrate the plasmid into their chromosomes and grow to form foci which, in turn, can be cloned and expanded into cell lines. This method can advantageously be used to engineer cell lines which express the gene protein product.

Any promoter may be used to drive the expression of the inserted gene. For example, viral promoters include but are not limited to the CMV promoter/enhancer, SV 40, papillomavirus, Epstein-Barr virus, elastin gene promoter and β-globin. If transient expression is desired, such constitutive promoters are preferably used in a non-integrating and/or replication-defective vector. Alternatively, inducible promoters could be used to drive the expression of the inserted gene when necessary. For example, inducible promoters include, but are not limited to, metallothionein and heat shock protein.

Examples of transcriptional control regions that exhibit tissue specificity for connective tissues which have been described and could be used, include but are not limited to: elastin or elastase I gene control region which is active in pancreatic acinar cells (Swit et al., 1984, Cell 38:639–646; Ornitz et al., 1986, Cold Spring Harbor Symp. Quant. Biol. 50:399–409; MacDonald, 1987, Hepatology 7:425–515). The deposition of elastin is correlated with specific physiological and developmental events in different tissues, including the vascular grafts. For example, in developing arteries, elastin deposition appears to be coordinated with changes in arterial pressure and mechanical activity. The transduction mechanisms that link mechanical activity to elastin expression involve cell-surface receptors. Once elastin-synthesizing cells are attached to elastin through cell-surface receptors, the synthesis of additional elastin and other matrix proteins may be influenced by exposure to stress or mechanical forces in the tissue (for example, the constant movement of the construct in the bioreactor) or other factors that influence cellular shape.

Once genetically engineered cells are implanted into an individual, the presence of TPA, streptokinase or urokinase activity can bring about amelioration of platelet aggregation, blood coagulation or thromboembolism. This activity is maintained for a limited time only, for example, to prevent potential complications that generally develop during the early phase after valve implantation, such as, platelet aggregation, blood clotting, coagulation or thromboembolism. Alternatively, once genetically engineered cells are implanted into an individual, the presence of the anti-inflammatory gene products, for example, peptides or polypeptides corresponding to the idiotype of neutralizing antibodies for TNF, IL-2, or other inflammatory cytokines, can bring about amelioration of the inflammatory reactions associated with diseases such as vascular, gastrointestinal, hernia or genitourinary tract disease.

The stromal cells used in the three-dimensional culture system of the invention may be genetically engineered to "knock out" expression of factors or surface antigens that promote clotting or rejection at the implant site. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to stromal cell can be reduced or knocked out using a number of techniques, for example, expression may be inhibited by inactivating the gene completely (commonly termed "knockout") using the homologous recombination technique. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. Mombaerts, P., et al., 1991, Proc. Nat. Acad. Sci. U.S.A. 88:3084–3087.

Antisense and ribozyme molecules which inhibit expression of the target gene can also be used in accordance with the invention to reduce the level of target gene activity. For example, antisense RNA molecules which inhibit the expression of major histocompatibility gene complexes (HLA) shown to be most versatile with respect to immune responses. Still further, triple helix molecules can be utilized in reducing the level of target gene activity. These techniques are described in detail by L. G. Davis, et al., eds, *Basic Methods in Molecular Biology,* 2nd ed., Appleton & Lange, Norwalk, Conn. 1994.

In another alternative, the stromal cells can be genetically engineered to block gene expression necessary for the transition of smooth muscle cells to proliferate, migrate and to lead to development of neointimal hyperplasia, e.g., by antisense oligodeoxynucleotide blockade of expression of cell division cycle 2 kinase and proliferating cell nuclear antigen. Mann, M. J., et al., 1995, Proc. Natl. Acad. Sci. U.S.A. 92:4502–4506.

Using any of the foregoing techniques, the expression of fibrinogen, von Willebrands factor, factor V or any cell surface molecule that binds to the platelet $\alpha 2B\beta$-3 receptor can be knocked out in the stromal cells to reduce the risk of clot formation in the vascular or other types of biological tissue grafts. Likewise, the expression of MHC class II molecules can be knocked out in order to reduce the risk of rejection of the graft.

In yet another embodiment of the invention, the three-dimensional culture system could be used in vitro to produce biological products in high yield. For example, a cell which naturally produces large quantities of a particular biological product (e.g., a growth factor, regulatory factor, peptide hormone, antibody, etc.), or a host cell genetically engineered to produce a foreign gene product, could be clonally expanded using the three-dimensional culture system in vitro. If the transformed cell excretes the gene product into the nutrient medium, the product may be readily isolated from the spent or conditioned medium using standard separation techniques (e.g., HPLC, column chromatography, electrophoretic techniques, to name but a few). A "bioreactor" has been devised which takes advantage of the flow method for feeding the three-dimensional cultures in vitro. Essentially, as fresh media is passed through the three-dimensional culture, the gene product is washed out of the culture along with the cells released from the culture. The gene product is isolated (e.g., by HPLC column chromatography, electrophoresis, etc.) from the outflow of spent or conditioned media.

The three-dimensional culture system of the invention may also afford a vehicle for introducing genes and gene products in vivo for use in gene therapies or to augment healing at the site of implantation. For example, using recombinant DNA techniques, a gene for which a patient is deficient could be placed under the control of a viral or tissue-specific promoter. Alternatively, DNA encoding a gene product that enhances wound healing may be engineered into the cells grown in the three-dimensional system. The recombinant DNA construct containing the gene could be used to transform or transfect a host cell which is cloned and then clonally expanded in the three-dimensional culture system. The three-dimensional culture which expresses the active gene product, could be implanted into an individual who is deficient for that product.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells. For example, genetically engineered cells that express the gene product could be incorporated into living stromal tissue tubes that can be used as blood vessels; in this case the gene product may be delivered to the bloodstream where it will circulate. Alternatively, genetically engineered cells that express wound healing factors may be incorporated into the living stromal cultures used to make tendons and ligaments to enhance wound healing at the site of implantation.

Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins (e.g., those characterized by abundant rough endoplasmic reticulum and golgi complex) are preferable. To this end, liver and other glandular tissues could be selected. When using liver cells, liver specific viral promoters, such as hepatitis B virus elements, could be used to introduce foreign genes into liver cells and regulate the expression of such genes. These cells could then be cultured in the three-dimensional system of the invention. Alternatively, a liver-specific promoter such as the albumin promoter could be used.

Examples of transcriptional control regions that exhibit tissue specificity which have been described and could be used, include but are not limited to: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:42S-51S); insulin gene control region which is active in pancreatic beta cells (Hanahan, 1985, Nature 315:115–122); immunoglobulin gene control region which is active in lymphoid cells (Grosschedl et al.,1984, Cell 38:647–658;.Adams et al., 1985, Nature 318:533–538; Alexander et al., 1987, Mol. Cell. Biol. 7:1436–1444); albumin gene control region which is active in liver (Pinkert et al., 1987, Genes and Devel. 1:268–276); alpha-fetoprotein gene control region which is active in liver (Krumlauf et al., 1985, Mol. Cell. Biol. 5:1639–1648; Hammer et al., 1987, Science 235:53–58); alpha-1-antitrypsin gene control region which is active in liver (Kelsey et al., 1987, Genes and Devel. 1:161–171); beta-globin gene control region which is active in myeloid cells (Magram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286); and gonadotropic releasing hormone gene control region which is active in the hypothalamus (Mason et al., 1986, Science 234:1372–1378).

In a further embodiment of the invention, three-dimensional cultures maybe used to facilitate gene transduction. For example, and not by way of limitation, three-dimensional cultures of fibroblast stroma comprising a recombinant virus expression vector may be used to transfer the recombinant virus into cells brought into contact with the stromal matrix, thereby simulating viral transmission in vivo. The three-dimensional culture system is a more efficient way of accomplishing gene transduction than are current techniques for DNA transfection.

In an alternate embodiment of the invention, the three-dimensional cultures may be used as model systems for the study of physiologic or pathologic conditions and the effect of drugs and treatments. For example, in a specific embodiment of the invention, a three-dimensional culture system may be used as a model for the blood-brain barrier; such a model system can be used to study the penetration of substances through barriers such as the blood-brain barrier, the glomerular apparatus, and mucosa of nasopharyngeal passage lining.

For purposes of description only, and not by way of limitation, sample embodiments of the invention are described below. For purposes of description only, and not by way of limitation, the formation of the three-dimensional cultures into tubes is described based upon the type of tissue and cells used in various systems. These descriptions specifically include but are not limited to tubular sections of gastrointestinal tract, genitourinary tract as well as blood vessels. It is expressly understood that the three-dimensional culture system can be used with other types of cells to form other types of tubular tissues, all of which tissues are encompassed by the invention.

6. TUBULAR BIOLOGICAL TISSUES

The three-dimensional culture system can be used to construct single and multi-layer tubular tissues in vitro. In accordance with the invention, these tubular structures can simulate tubular tissues and organs in the body, including, but not limited to, blood vessels, gastrointestinal tract and genitourinary tract.

The different biological structures described below have several features in common. They are all tubular structures primarily composed of layers of stromal tissue with an interior lining of epithelium (gastrointestinal and genitourinary) or endothelium (blood vessels). Their connective tissues also contain layers of smooth muscle with varying degrees of elastic fibers, both of which are especially prominent in arterial blood vessels. By including and sustaining these components in three-dimensional cultures according to the present invention, the tissues they compose can attain the special structural and functional properties they require for proper physiological functioning in vivo. They can then serve as replacements for damaged or diseased tubular tissues in a living body.

6.1. Single Mesh Layer Tubes

The following subsections describe the use of a mesh framework to support the growth of the living stromal tissue used to prepare tubes that can be implanted into the body.

6.1.1. Flat Mesh Starting Material

A mesh can be cut into a rectangular strip of which the width is approximately equal to the inner circumference of the tubular organ into which it will ultimately be inserted. The cells can be inoculated onto this mesh and incubated by floating or suspending in liquid media. At the appropriate stage of confluence, the mesh can be rolled up into a tube by joining the long edges together. The seam can be closed by suturing the two edges together using fibers of a suitable material of an appropriate diameter.

6.1.2. Tubular Mesh Starting Material

According to the invention, a mesh can be woven as a tube, inoculated with stromal cells and suspended in media in an incubation chamber. In order to prevent cells from occluding the lumen, one of the open ends of the tubular mesh can be affixed to a nozzle. Liquid media can be forced through this nozzle from a source chamber connected to the incubation chamber to create a current through the interior of the tubular mesh. The other open end can be affixed to an outflow aperture which leads into a collection chamber, from which the media can be recirculated through the source chamber. The tube can be detached from the nozzle and outflow aperture when incubation is complete. This method is described by Ballermann, B. J., et al., Int. Application No. WO 94/25584 and in a pending application entitled, "APPARATUS AND METHOD FOR STERILIZING, SEEDING, CULTURING, STORING, SHIPPING AND TESTING TISSUE, SYNTHETIC, OR NATIVE VASCULAR GRAFTS," filed Apr. 27, 1995 by Peterson, A., et al. (Advanced Tissue Sciences, Inc.), Ser. No. 08/430,768, both of which are incorporated herein by reference in its entirety.

6.2. Multiple Mesh Layers Tubes

In general, two three-dimensional cultures can be combined into a tube in accordance with the invention using any of the following methods.

6.2.1. Multiple Flat Meshes

One flat rectangular culture can be laid atop another and sutured together. This two-layer sheet can then be rolled up, as described above for a single culture in Section 6.1.1, by joining together the long edges, and securing with sutures.

6.2.2. Flat Meshes Wrapped Around Tubular Meshes

One tubular mesh that is to serve as the inner layer can be inoculated and incubated. A second mesh can be grown as a flat, rectangular strip with width slightly larger than the outer circumference of the tubular mesh. After appropriate growth is attained, the rectangular mesh can be wrapped around the outside of the tubular mesh. Closing the seam of the outer strip and securing it to the inner tube can be accomplished in a single suturing step.

6.2.3. Multiple Tubular Meshes

Two tubular meshes of slightly differing diameters can be grown separately. The culture with the smaller diameter can be inserted inside the larger one, and secured with sutures. This method would not be practical for very narrow tubes.

For each of these methods, more layers can be added by reapplying the method to the double layered tube. The meshes can be combined at any stage of growth of the culture they contain, and incubation of the combined meshes can be continued when desirable.

According to the present invention, any suitable method can be employed to shape the three-dimensional culture to take on the conformation of the natural organ or tissue to be simulated.

The descriptions which follow are provided to demonstrate how to construct model tubular tissues and organs in vitro. In each case, one or more stromal layers can be established as described in section 5.1. Particular attention is paid to generating the specialized properties of specific natural connective tissues by including and maintaining the materials inherent to those natural tissues in the three-dimensional cultures. One or more surface layers of generally more homogenous cellular composition (such as endothelium, epithelium, or smooth muscle) can then be cultured onto the stromal layer as described in Section 5.2. Using the methods outlined above in this section, these three-dimensional cultures can be shaped to assume a tubular conformation which simulates the shape of a natural tubular organ or tissue. Variations of this basic approach can be used to better simulate the natural organs and tissues to be corrected.

These tubular constructions simulate biological structures in vivo and may be readily implanted to replace damaged or diseased tissues. However, the invention encompasses the three-dimensional cultures described herein in any possible form and does not require that these cultures be formed into tubes. Flat three-dimensional cultures can be implanted, for example, directly into the body to replace any part or all of the circumference of a tubular structure, depending on the extent of replacement required.

7. BLOOD VESSELS

The replication of blood vessel elements in vitro is described below in particular for arteries and veins.

7.1. Arteries

Arteries are tubes lined with a thin layer of endothelial cells and generally composed of three layers of connective tissue: the intima (which is not present in many muscular arteries, particularly smaller ones), media, and adventitia, in order from inside to outside.

The main cellular component of the inner two layers is an undifferentiated smooth muscle cell, which produces the extracellular protein elastin. The internal elastic lamina, which lies just interior to the media, is a homogenous layer of elastin. The abundance of elastin in their walls gives arteries the ability to stretch with every contraction of the heart. The intima and media also contain some fibroblasts, monocytes, and macrophages, as well as some collagen.

The adventitia is composed of more ordinary connective tissue with both elastic and collagenic fibers. Collagen in this layer is import ant in preventing over-stretching.

While all the layers of the arterial wall are connective tissue, there is a compositional and functional difference between the adventitia and the inner two coats, the intima and the media. Consequently, it may be advantageous in accordance with the invention to grow these different layers in separate meshes. Whether the intima and media are grown in separate meshes, or combined in one, depends on how distinct these layers are in the particular artery into which the three-dimensional culture is to be implanted.

For example, according to the invention fibroblasts can be isolated from the adventitia of a patient's artery and used to inoculate a three-dimensional matrix, as described in Section 6.1, and grown to subconfluence. Cells can be isolated from tissue rich in elastin-producing undifferentiated smooth muscle cells, also containing some fibroblasts, from the intima and media of the same artery. These cells can be used to inoculate a separate mesh and grown to subconfluence. Once the elastin-producing cells have proliferated to the appropriate extent, these meshes can be combined using one of the methods detailed in Section 6.2. In this manner, the smooth muscle cells can proliferate and produce elastin in a three-dimensional environment that simulates that of natural arterial walls.

Endothelial cells can be isolated from the same patient. When the two cultures reach the appropriate degree of confluence, the endothelial cells can be seeded on top of the upper, elastin-rich layer and incubated until they form a confluent layer.

If a fully functional replacement with all the various layers of tissue is not required, a simple homogenous three-dimensional elastin-rich stromal culture can be used. Alternatively, the stromal culture could be lined with endothelium. More layers of this homogenous stromal matrix can be combined to provide the appropriate thickness for such a prosthesis.

7.2. Veins

The layers of the connective tissue comprising the walls of veins are less well delineated than those of arteries, and contain much more collagen and less elastin. Consequently, a single three-dimensional culture can be grown, for example, from a single inoculum of cells. These cells consisting mostly of fibroblasts with some smooth muscle cells, can be isolated from the walls of a vein of the patient. When the appropriate degree of confluence is reached, endothelial cells, isolated from the same patient, for example, can be seeded on top of the stromal layer and grown to confluence.

8. GASTROINTESTINAL TRACT

Another embodiment of the invention provides for the replication of gastrointestinal tract elements in vitro in a system comparable to physiological conditions. The gastrointestinal tract comprises several different organs, but all have the same general histological scheme.

1. Mucous Membrane: The mucous membrane is the most interior layer of the gastrointestinal tract, and is composed of three sub-layers. The absorptive surfaces particularly are highly folded to increase the surface area. The lumen is lined with a thin layer of epithelium, which is surrounded by the lamina propria, a connective tissue which contains fibroblasts, some smooth muscle, capillaries, as well as collagenic, reticular, and some elastic fibers. Lymphocytes are also found here to protect against invasion, especially at absorptive surfaces where the epithelium is thin. The third sub-layer, the muscularis mucosa, consists of two thin layers of smooth muscle with varying amounts of elastic fibers. The smooth muscle fibers of the inner layer are arranged circularly, and the outer layer is arranged longitudinally.

2. Submucosa: This layer consists of loose connective tissue including elastic fibers as well as larger blood vessels and nerve fibers.

3. Muscularis Externa: This layer consists of two thick layers of smooth muscle which provide the motion which advances material along through the gastrointestinal tract. The muscle fibers of the inner layer are arranged circularly, while in the outer layer they are longitudinal. An exception is the upper third of the esophagus, which contains striated muscle allowing for the voluntary contractions associated with swallowing.

4. Serosa (or Adventitia): This outermost layer consists of loose connective tissue, covered by squamous mesothelium where the tract is suspended freely.

These four layers can be constructed in vitro in accordance with the invention by making different three-dimensional tubular tissue cultures. For example, in order to construct the mucous membrane, a mesh composed of bioabsorbable material can be inoculated with fibroblasts, smooth muscle cells, and other cells isolated from the lamina propria of the patient who is to receive the implant, from a section of tract in or around the site that is to be replaced. If the site of transplantation is an absorptive surface, the mesh can be contoured on the surface which is to face the lumen.

Simultaneously, a second mesh whose inner circumference is slightly larger than the outer circumference of the first mesh can be inoculated with the fibroblasts and other cells of the patient's submucosal layer. Similarly, a third mesh can be inoculated with cells from the serosa. These meshes can be configured and incubated as outlined in section 7.1.

When each stromal layer has grown to the appropriate extent, the respective surface layers can be cultured. For example, epithelial cells can be seeded onto the top (or interior, if already tubular) of the lamina propria mesh, and smooth muscle cells can be seeded onto the bottom (or exterior, if already tubular) of the same mesh to form the muscularis mucosa.

In parallel, cells isolated from the muscularis externa can be seeded onto the surface of the submucosa, or the surface of the serosa, or both. Alternatively, the inner layer of the muscularis externa can be grown on the submucosal stromal mesh, and the outer layer can be grown on the serosal stromal mesh.

At appropriate stages of growth, these meshes can be combined using one of the methods outlined in Section 7.2. The cultures can be incubated until the surface layers are mature.

During the assembly of the different three-dimensional cultures, vascular tissue (i.e., arteries and veins) can be added to the tubular construct. For example, a blood vessel can be constructed in vitro as outlined in Section 8. Before combining the submucosal and serosal meshes, this blood vessel can be laid down longitudinally along one or both surfaces of the submucosal stromal culture. Upon implantation, it can be spliced to the appropriate blood vessel of the adjoining segment of the gastrointestinal tract.

By growing these layers separately, and then combining them and allowing further growth, distinct tissue layers can be formed and then allowed to mature in the same type of environment as naturally allows for their specialization.

In cases where only one of these layers has been damaged in the patient, a single three-dimensional culture would suffice, and can be implanted selectively to replace just that layer.

If a fully functional replacement with all the various layers of tissue is not required, a simple homogenous three-dimensional stromal culture lined with epithelium can be used. More layers of this homogenous stromal matrix can be combined to provide the appropriate thickness for such a prosthesis.

9. GENITOURINARY TRACT

Another embodiment of the invention provides for the replication of genitourinary tract elements in vitro in a system comparable to physiological conditions. The genitourinary tract is very similar to the digestive tract in terms of histology. The primary differences can be the smaller diameters and lack of absorptive surface of the genitourinary vessels.

9.1. Ureter

Like the gastrointestinal tract, the ureter also has a mucous membrane as its inner layer. Despite not having an absorptive surface, the interior surface of the ureter is highly folded to form a stellate conformation in cross-section. The epithelial lining, however, is four to five cells thick. The lamina propria, which lies beneath the epithelium, contains abundant collagen, some elastin, and occasional lymph nodules.

Surrounding the mucous membrane is a muscular coat, whose inner layer contains longitudinally arranged smooth muscle fibers, while those of the outer layer are circularly arranged. The outermost layer, the adventitia, consists of fibroelastic connective tissue.

In order to construct a simulation of a ureter in accordance with the invention, stromal cells can be isolated from the two connective tissues associated with the ureter and used to initiate two separate three-dimensional cultures as described in Section 6.1. After appropriate growth of the stromal layers, epithelial cells can be seeded on the interior side of the lamina propria derived culture, and smooth muscle cells can be seeded onto the opposite surface. In parallel, smooth muscle cells can be seeded onto one surface of the adventitia derived culture. The two three-dimensional cultures can then be combined to form one tubular structure, as described in Section 6.2., and incubated until the surface layers are mature.

If a fully functional replacement with all the various layers of stromal tissue is not required, a simple homogenous three-dimensional stromal culture lined with epithelium can be used. More layers of this homogenous stromal matrix can be combined to provide the appropriate thickness for such a prosthesis.

9.2. Urethra

The urethra consists simply of a lamina propria which is lined with epithelium and surrounded by two layers of smooth muscle fibers. In the inner layer, the fibers are arranged longitudinally, while in the outer layer they are circular. The connective tissue of the lamina propria is rich in elastic fibers and contains many venules.

Since the urethra has only one stromal layer, a single three-dimensional culture may suffice for its construction in vitro in accordance with the invention. A mesh can be inoculated, for example, with cellular material isolated from the patient's urethral lamina propria as described in section 7.1. At the appropriate stage of confluence, epithelial cells can be seeded onto one surface (interior) and smooth muscle can be seeded onto the opposite surface (exterior). The three-dimensional culture can be incubated until the surface layers are mature.

10. HERNIA REPAIR

In herniorrhaphy, a corrective bioresorbable three-dimensional mesh, seeded with fibroblast cells could be used. Alternatively, cells might be seeded onto a synthetic mesh substrate for stronger fascial closure.

11. FORMATION OF TENDONS AND LIGAMENTS

Ligaments and tendons consist of fibroblasts surrounded by fibers of collagen type I and III and a predominance of the glycosaminoglycan dermatan sulfate. The embodiment of the invention provides for the placement of stromal tissue under mechanical or pulsatile forces to alter the formation and alignment of collagen fibers into bundles more dense and parallel than those routinely seen in dermis. By placing dermal fibroblasts on polymers and growing the tissues under increasing pulsing mechanical force, the final structure will have the tensile strength of a normal tendon ($\approx 33$ MPa). Ligamentous or tendinous structures are also created utilizing similar methods with the option of attaching tissue-engineered bone to the end of the forming ligament or tendon in order to provide an attachment site.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A three-dimensional pancreatic culture comprising pancreatic parenchymal cells cultured on a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells.

2. The three-dimensional cell culture of claim 1 in which the parenchymal cells are pancreatic endocrine cells.

3. The three-dimensional cell culture of claim 2 in which the pancreatic endocrine cells are islet of Langerhans cells.

4. The three-dimensional cell culture of claim 1 in which the parenchymal cells are pancreatic exocrine cells.

5. The three-dimensional pancreatic culture of claim 1 in which the pancreatic parenchymal cells comprise a combination of exocrine and endocrine cells.

6. The three-dimensional cell culture of claim 5 in which the pancreatic exocrine cells are acinar cells.

7. The three-dimensional cell culture of claims 1, 2, 3, 4, or 6 in which the parenchymal cells are genetically engineered cells.

8. The three-dimensional cell culture of claim 1 in which the stromal cells are fibroblasts.

9. The three-dimensional cell culture of claim 1 in which the stromal cells are a combination of fibroblasts and endothelial cells, pericytes, macrophages, monocytes, leukocytes, plasma cells, mast cells or adipocytes.

10. The three-dimensional cell culture of claim 1 in which the framework is composed of a biodegradable material.

11. The three-dimensional cell culture of claim 10 in which the biodegradable material is cotton, polyglycolic acid, cat gut sutures, cellulose, gelatin, or dextran.

12. The three-dimensional cell culture of claim 1 in which the framework is composed of a non-biodegradable material.

13. The three-dimensional cell culture of claim 12 in which the non-biodegradable material is a polyamide, a polyester, a polystyrene, a polypropylene, a polyacrylate, a polyvinyl, a polycarbonate, a polytetrafluorethylene, or a nitrocellulose compound.

14. The three-dimensional cell culture of claim 10, 11, 12 or 13 in which the framework is pre-coated with collagen.

15. The three-dimensional cell culture of claim 1, 2, 3, 4, 6, 8, 9, 10 or 13 in which the framework is a mesh.

16. The three-dimensional cell culture of claim 7 in which the framework is a mesh.

17. The three-dimensional cell culture of claim 14 in which the framework is a mesh.

18. The three-dimensional pancreatic culture of claim 1 in which the pancreatic parenchymal cells comprise pancreatic stem cells.

19. The three-dimensional pancreatic culture of claim 1 in which the stromal cells comprise umbilical cord cells, placental cells, mesenchymal stem cells or fetal cells.

20. A method for culturing pancreatic cells in vitro, comprising culturing pancreatic parenchymal cells inoculated onto a living stromal tissue prepared in vitro, comprising the stromal cells and connective tissue proteins naturally secreted by the stromal cells attached to and substantially enveloping a framework composed of a biocompatible, non-living material formed into a three-dimensional structure having interstitial spaces bridged by the stromal cells.

21. The method of claim 20 in which the parenchymal cells are pancreatic endocrine cells.

22. The method of claim 21 in which the pancreatic endocrine cells are islet of Langerhans cells.

23. The method of claim 20 in which the parenchymal cells are pancreatic exocrine cells.

24. The method of claim 20 in which the pancreatic parenchymal cells comprise a combination of exocrine and endocrine cells.

25. The method of claim 24 in which the pancreatic exocrine cells are acinar cells.

26. The method of claim 20, 21, 22, 23 or 25 in which the parenchymal cells are genetically engineered cells.

27. The method according to claim 20 in which the stromal cells are fibroblasts.

28. The method according to claim 20 in which the stromal cells are a combination of fibroblasts and endothelial cells, pericytes, macrophages, monocytes, leukocytes, plasma cells, mast cells or adipocytes.

29. The method according to claim 20 in which the framework is composed of a biodegradable material.

30. The method according to claim 29 in which the biodegradable material is cotton, polyglycolic acid, cat gut sutures, cellulose, gelatin, or dextran.

31. The method according to claim 20 in which the framework is composed of a non-biodegradable material.

32. The method according to claim 31 in which the non-biodegradable material is a polyamide, a polyester, a polystyrene, a polypropylene, a polyacrylate, a polyvinyl, a polycarbonate, a polytetrafluorethylene, or a nitrocellulose compound.

33. The method according to claim 29, 30, 31, or 32 in which the framework is pre-coated with collagen.

34. The method according to claim 20, 21, 22, 23, 25, 27, 28, 29, 30, 31 or 32 in which the framework is a mesh.

35. The method according to claim 26 in which the framework is a mesh.

36. The method according to claim 33 in which the framework is a mesh.

37. The method of claim 20 in which the pancreatic parenchymal cells comprise pancreatic stem cells.

38. The method of claim 20 in which the stromal cells comprise umbilical cord cells, placental cells, mesenchymal stem cells or fetal cells.

* * * * *